United States Patent [19]

Mizuno

[11] Patent Number: 4,607,163
[45] Date of Patent: Aug. 19, 1986

[54] DEVICE FOR COUPLING A LIQUID CHROMATOGRAPH AND A MASS SPECTROMETER

[75] Inventor: Tokuo Mizuno, Tokyo, Japan

[73] Assignee: JEOL Ltd., Tokyo, Japan

[21] Appl. No.: 681,603

[22] Filed: Dec. 14, 1984

[30] Foreign Application Priority Data

Dec. 19, 1983 [JP] Japan ................. 58-239459

[51] Int. Cl.$^4$ ............................................. B01D 59/44
[52] U.S. Cl. ..................................... 250/281; 250/281
[58] Field of Search ............. 250/281, 282, 283, 288, 250/423 R; 73/61.1 C

[56] References Cited

U.S. PATENT DOCUMENTS

| 4,209,696 | 6/1980 | Fite | 250/288 |
| 4,239,967 | 12/1980 | Carr et al. | 250/281 |
| 4,298,795 | 11/1981 | Takeuchi et al. | 250/282 |

Primary Examiner—Bruce C. Anderson
Attorney, Agent, or Firm—Webb, Burden, Robinson & Webb

[57] ABSTRACT

An instrument combining a mass spectrometer with a liquid chromatograph has a low-pressure chamber that is evacuated by an evacuating equipment, an exit nozzle for allowing the effluent from the chromatograph to be ejected as a jet into the low-pressure chamber, and a connecting passage for conveying the jet of the effluent from the nozzle into the ionization chamber of the mass spectrometer, to stably supply the effluent from the chromatograph as the sample for the ion source into the ionization chamber. The instrument is further provided with a means for producing a flow of gas which moves along the inner walls of the low-pressure chamber and the connecting passage in such a way that the jet of the effluent is enveloped in the gas flow.

8 Claims, 6 Drawing Figures

DEVICE FOR COUPLING A LIQUID CHROMATOGRAPH AND A MASS SPECTROMETER

BACKGROUND OF THE INVENTION

The present invention relates to a device for coupling a liquid chromatograph and a mass spectrometer.

Chromatographs are effective apparatus for separating and analyzing mixture samples containing different components. When a mass spectrometer is connected as a detecting means to the chromatograph, a large amount of information about molecular weights and molecular structures can be obtained. It is relatively easy to connect a mass spectrometer to a gas chromatograph, and this combination has been extensively used to date. However, an instrument combining a mass spectrometer with a liquid chromatograph requires various considerations, because liquid must be introduced into the high-vacuum mass spectrometer. It is difficult to attain a satisfactory performance. Accordingly, the combination of a liquid chromatograph and a mass spectrometer is less widely used than the combined gas chromatograph/mass spectrometer.

A prior art instrument combining a mass spectrometer with a liquid chromatograph is shown in FIG. 1. The chromatograph 1 is indicated schematically. The mass spectrometer has an ionization chamber 2 which is formed in an ion source block 4. The outer wall of the ion source is indicated by numeral 3. Mounted between the ionization chamber 2 and the chromatograph 1 is an interface body 5 having a chamber 6 which is evacuated to a low pressure by a vacuum pump 7. In this body 5, a feed nozzle 8 is disposed opposite to a receiver nozzle 9. The feed nozzle 8 is connected to the chromatograph 1, while the receiver nozzle 9 is connected to the ionization chamber 2. The feed nozzle 8 consists of a dual tube 10 and an apertured plate 11 disposed at the front end of the tube 10. The effluent from the chromatograph 1 is conveyed through the inner tube of the double tube 10 to the position of the plate 11 at the front end. Then, the effluent is partially ejected toward the receiver nozzle 9 through the apertured plate 11. The remaining effluent is moved out of the low-pressure chamber through the outer tube of the double tube 10, and then discharged via a discharge tube 12 and a flow control valve 13. The receiver nozzle 9 is connected to the ionization chamber 2 by means of a passage 14, which is heated by a heater 15.

The device of FIG. 1 must operate in such a way that the jet of the effluent from the feed nozzle 8 travels straightly and correctly into the receiver nozzle 9. If the jet does not move straight, it will collide with the inner wall of either the connecting passage 14 or the chamber 6 or the end of the receiver nozzle 9, resulting in the thermal decomposition of the sample or local cooling of the bombarded part. In the latter case, ice or front columns grow and clog up the connecting passage, deteriorating the rate of passage of the sample. However, since the diameter of the hole of the feed nozzle 8 is quite small, a slight change in the conditions in that portion necessarily disturbs the direction of the jet. Hence, the occurrence of the aforementioned undesired phenomena has been unavoidable. Another prior art system of combined liquid chromatograph/mass spectrometer is described in U.S. Pat. No. 4,298,795.

SUMMARY OF THE INVENTION

It is the main object of the present invention to provide an instrument in which a jet of effluent can be introduced into the ionization chamber without contacting the surrounding wall surface even if the jet slightly deviates from the intended direction.

This object is achieved in accordance with the teachings of the present invention by a device which couples a mass spectrometer with a liquid chromatograph and which comprises a chamber that is evacuated to a low pressure by evacuating equipment, feed nozzle for introducing the effluent from the chromatograph as a jet into the low-pressure chamber, and a connecting passage for conveying the jet of effluent emitted from the nozzle to the ionization chamber of the mass spectrometer. The coupling device is characterized by the provision of a means for generating a flow of gas that moves along the inner walls of the low-pressure chamber and the connecting passage in such a way that the jet of the effluent is enveloped in the gas flow.

DESCRIPTION OF THE PREFERRED EMBODIMENTS

Figure 1:
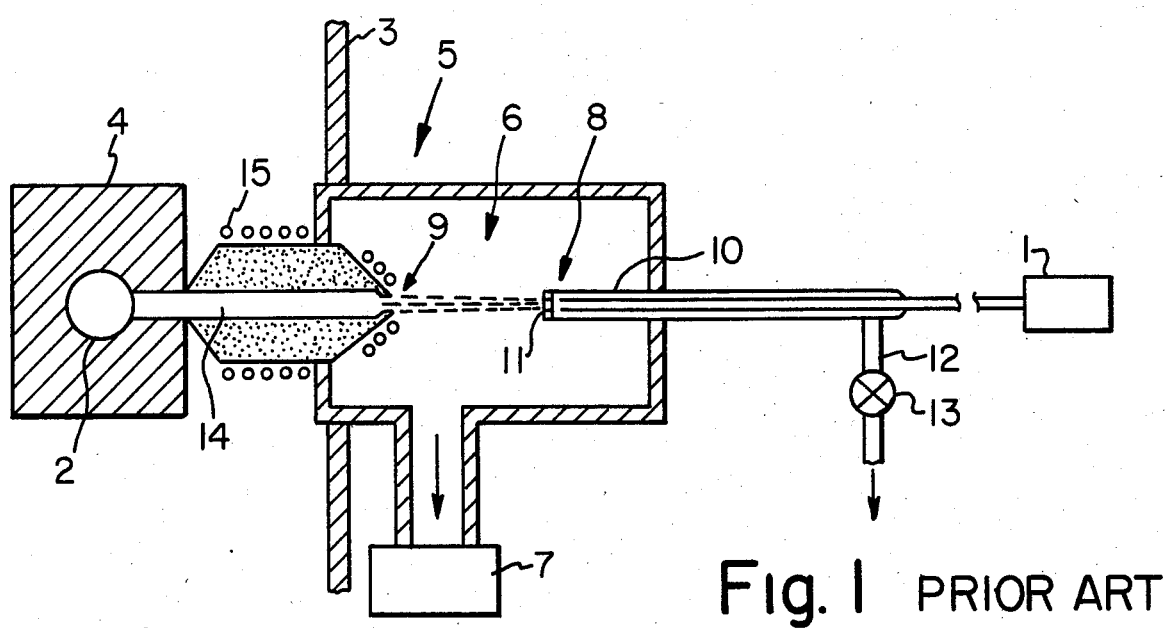
FIG. 1 is a schematic diagram of the main portion of conventional combined liquid chromatograph/mass spectrometer.
Figure 2:
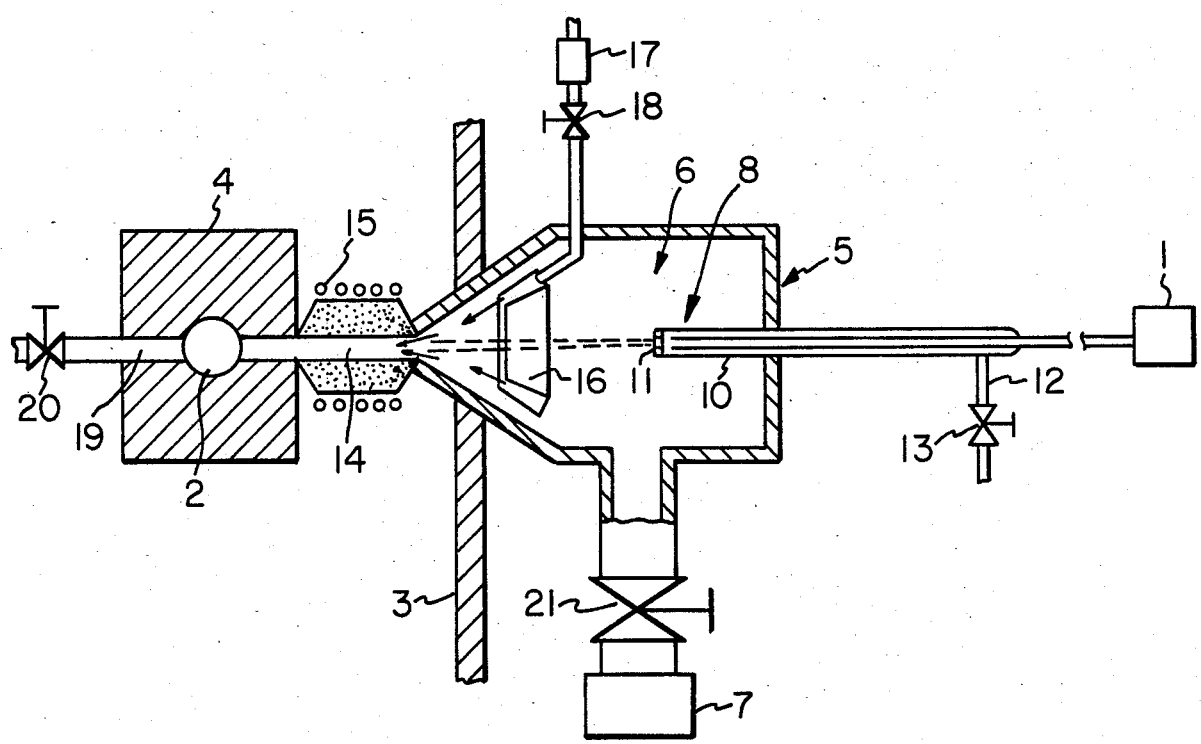
FIG. 2 is a schematic diagram of the main portion of combined liquid chromatograph/mass spectrometer according to the present invention.

FIG. 2 is a schematic diagram in cross section showing the main portion of an instrument according to the invention. It is to be noted that those components which are the same as those in FIG. 1 are indicated by the same reference numerals as in FIG. 1. In the instrument of FIG. 2, the low-pressure chamber 6 has a connecting portion that tapers such that the gas inside the chamber 6 can smoothly flow into the connecting passage 14. An annular nozzle 16 is provided which surrounds the passageway for the jet of effluent from the exit nozzle 8. The port of the nozzle 16 faces to the passage 14. An auxiliary gas is heated by a heater 17 to an appropriate temperature, and then it is supplied via a flow control valve 18. The inside of the ionization chamber 2 is evacuated through an evacuating passage 19 that is connected to a suitable vacuum pump (not shown) via a flow control valve 20. A further flow control valve 21 is inserted between the vacuum pump 7 and the low-pressure chamber 6.

In the structure of FIG. 2, the annular nozzle 16 produces a flow of gas that moves toward the ionization chamber 2 along the inner walls of the low-pressure chamber and the connecting passage in such a way that the jet of the effluent is enveloped in the gas flow. Therefore, the jet that is guided by the surrounding gas flow is smoothly introduced into the ionization chamber 2 together with the gas flow without making contact with the surrounding wall, even if the jet deviates slightly from its intended direction. The introduced effluent component can be ionized by chemical ionization within the ionization chamber 2 by supplying a gas that is normally used for chemical ionization, such as $NH_3$ or $CH_4$, into the nozzle 16. With respect to chemical ionization, see "Journal of HRC & CC", Vol. 3, January 1980, pp.16–20.

The chemical ionization requires that the pressure inside the ionization chamber 2 be relatively strictly set. Control of the flow control valve 18 or 20 or both makes it possible to set the pressure inside the ionization chamber 2 to a range appropriate for chemical ionization. The pressure inside the ionization chamber also can be changed by adjusting the valve 21.

Figure 3:
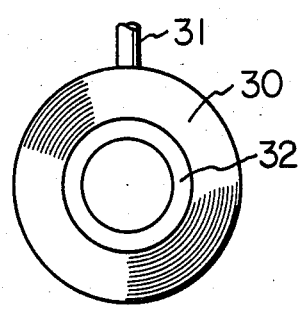
FIG. 3 is a front view of an annular nozzle useful in the practice of this invention.
Figure 4:
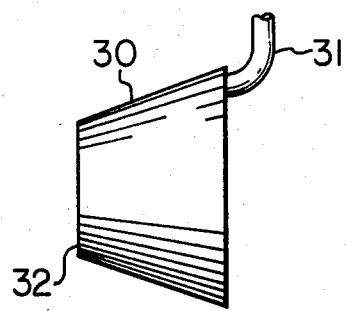
FIG. 4 is a side view of the same nozzle.

Referring now to FIGS. 3 and 4, the annular nozzle may comprise a plenum between two truncated conical surfaces. The outer conical surface 30 is shown in the drawings. A supply tube 31 feeds the plenum. At the small end of the plenum is an annular opening 32 from which a cone shaped flow of gases emerges during use.

Figure 5:
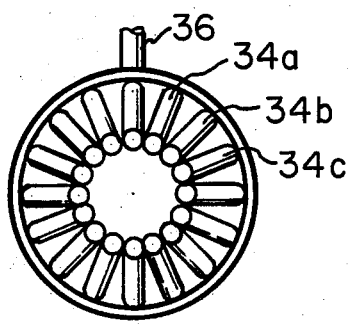
FIG. 5 is a front view of a nozzle comprised of a plurality of thin pipes.
Figure 6:
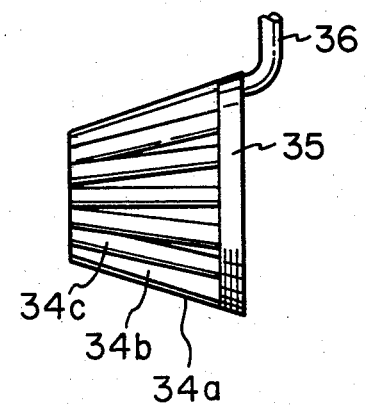
FIG. 6 is a side view of the same nozzle.

As a modified embodiment (see FIGS. 5 and 6), a nozzle consisting of a plurality of thin pipes 34a, 34b, 34c arranged annularly may be used instead of the annular nozzle. The pipes connect to an annular plenum 35 which in turn connects to the supply tube 36. This modified embodiment yields the same advantages as the embodiment shown in FIG. 2.

In order to simply the instrument further, the evacuating means for the ion source may be made to communicate with the low-pressure chamber via the connecting passage 14 for evacuating the chamber, rather than the vacuum pump 7 that evacuates the chamber independently of the above-mentioned evacuating means.

I claim:

1. A device for coupling a liquid chromatograph and a mass spectrometer comprising a low-pressure chamber in communication with means for evacuating the chamber, an exit nozzle opening into said chamber for ejecting the effluent from the chromatograph as a jet, a connecting passage opening into said chamber for conveying the jet of the effluent emitted from the nozzle into the ionization chamber of the mass spectrometer, and a means for producing a flow of gas which moves along the inner walls of the low-pressure chamber in the vicinity of the connecting passage and along the walls of the connecting passage in such a way that the jet of the effluent is enveloped in the gas flow and the effluent does not contact the walls.

2. The device of claim 1 wherein the means for producing the gas flow comprises an annular nozzle.

3. The device of claim 1 wherein the means for producing the gas flow comprises a nozzle consisting of a plurality of thin pipes arranged annularly.

4. The device of claim 1 wherein the low-pressure chamber is directly evacuated by a vacuum pump provided independently.

5. The device of claim 1 wherein the low-pressure chamber is evacuated by the evacuating pump for the ion source of the mass spectrometer and is in communication with this evacuating pump via the connecting passage.

6. The device of claim 1 wherein the gas of the flow produced by the gas flow producing means is the source of the reactant gas for chemical ionization.

7. the device of claim 6 wherein the gas is the source of $NH_3$ or $CH_4$.

8. The device of claim 1 wherein the low-pressure chamber has an inner surface that tapers to the opening of the connecting passage.

* * * * *